United States Patent [19]

DeLuca

[11] 4,031,882
[45] June 28, 1977

[54] APPARATUS FOR INTERFACING TO ANATOMIC SIGNAL SOURCES

[75] Inventor: Carlo J. DeLuca, Newton, Mass.

[73] Assignee: Liberty Mutual Insurance Company, Boston, Mass.

[22] Filed: June 28, 1976

[21] Appl. No.: 700,195

Related U.S. Application Data

[62] Division of Ser. No. 595,582, July 14, 1975.

[52] U.S. Cl. .......................... 128/2.1 R; 128/2.1 E; 128/DIG. 4
[51] Int. Cl.² ........................................... A61B 5/04
[58] Field of Search ......... 128/2.1 R, 2.1 M, 2.1 E, 128/2.1 A, DIG. 4, 404, 418, 419 C, 419 P

[56] References Cited

UNITED STATES PATENTS

| | | | |
|---|---|---|---|
| 3,157,181 | 11/1964 | McCarty | 128/404 |
| 3,336,919 | 8/1967 | Russ | 128/2.1 E |
| 3,722,005 | 3/1973 | Cowland | 128/2.1 E |
| 3,737,579 | 6/1973 | Bolduc | 128/418 |
| 3,916,876 | 11/1975 | Freeman | 128/2.1 M |
| 3,957,036 | 5/1976 | Normann | 128/2.1 R |

OTHER PUBLICATIONS

Pollak, "The Waveshape . . . of EMG Needles", Med. & Biol. Eng., vol. 9, pp. 657–664, 1971.
Sonn et al., "A Prototype flexible microelectrode . . . applications", Med. & Biol. Eng., pp. 778–790, Nov. 1974.

*Primary Examiner*—William E. Kamm
*Assistant Examiner*—Lee S. Cohen
*Attorney, Agent, or Firm*—John E. Toupal

[57] ABSTRACT

A device for anatomic implantation to provide electrical interface to nerves. Included in the device are a pair of electrical leads secured to a coupling formed from a piece of woven sheet material, and having ends connected to spaced apart input terminals disposed adjacent to an inner surface of the coupling. Connected to the opposite ends of the leads are output terminals for interfacing to electrical recording or measuring instruments. The input terminals receive desired nerve signals while other unwanted anatomic signals are rejected by an insulative case that covers the woven coupling.

5 Claims, 12 Drawing Figures

APPARATUS FOR INTERFACING TO ANATOMIC SIGNAL SOURCES

CROSS-REFERENCE TO RELATED APPLICATION

This invention is a division of my co-pending U.S. application Ser. No. 595,582, filed July 14, 1975.

BACKGROUND OF THE INVENTION

This invention relates generally to a method and apparatus for interfacing to nerves and, more particularly, to a method and apparatus for obtaining electrical signals from the nervous system.

Prosthetic devices have been developed that use self-generated electrical signals as control signals. For example, the "Boston Arm", an above-elbow prosthesis that performs flexion and extension of the elbow, uses the myoelectric signals (EMG) from the biceps and triceps muscles to control a movement that these prime-mover muscles naturally performed in the pre-amputated limb. Although such control is useful to the amputee, it would be desirable to increase the mobility of the Boston Arm by incorporating additional controlled movements (such as pronation, supination, opening and closing of the hand) in the artificial limb. Unfortunately, the muscles normally controlling these functions are in the forearm and hand and, therefore, they are no longer present in above-elbow amputees. However, the nerves (median, radial, ulnar and musculocutaneous) that contained the motor neurons to these muscles are accessible in the remaining part of the arm. Thus, improved control of the Boston Arm could be achieved by obtaining chronic direct accessibility to the electrical signals in the peripheral nervous system. The ultimate objective would be to chronically obtain distinguishable nerve signals associated with functionally distinct movements of a limb. It would then be possible to use the nerve signals to activate and control an upper-limb prosthesis with multiple degrees of freedom.

Previous attempts to record voluntarily elicited nerve signals for the expressed purpose of controlling a prosthesis have encountered technical and physiological restrictions that prevented the recording of reliable signals. Attainment of such signals requires electrical interface to the nerve with an electrical device capable of; a good mechanical connection with the nerve trunk to minimize the relative movement of the electrode and nerve; providing a good signal-to-noise ratio; disregarding the concurring EMG signals from adjacent muscles; and causing minimum physical damage and few physiological restrictions to the nerve. Furthermore, all the materials used to construct the device must be biocompatible and have sufficient structural ruggedness to remain operational for lengthy periods of use.

The object of the invention, therefore, is to provide an electrical device for obtaining chronic direct accessibility to the electrical signals in the peripheral nervous system without contamination from other sources.

SUMMARY OF THE INVENTION

The present invention encompasses a system and a method for obtaining improved quality electrical signals generated anatomically. Included in the system are primary terminals suitable for implantation so as to pick up a physiologically generated primary signal comprising both a desired component derived from a primary tissue source and a noise component derived from an auxiliary tissue source. Also included are auxiliary terminals suitable for implantation directly adjacent to the primary terminals so as to pick up an anatomically generated auxiliary signal derived from the auxiliary signal source. Electrical leads connect the primary and auxiliary terminals and an output circuit having a processor for differentially combining the primary and auxiliary signals. By obtaining and then differentially combining both the primary and auxiliary signals there is obtained a high quality output signal corresponding to the desired component of the primary signal.

Use of the system entails anatomically implanting the primary terminals in locations that establish an electrical coupling with the primary tissue source in which the desired signal component is generated. The auxiliary terminals also are anatomically implanted closely adjacent to the primary terminals so as to establish electrical coupling with auxiliary tissue in which a noise component of the primary signal is available. The derived signals are fed out of the body by implanted electrical leads to output terminals which, in turn, feed the signals into the external output circuit wherein differential combination of the signals occurs.

In a preferred embodiment of the invention, the primary and auxiliary terminals are mounted on a coupling device formed from a hollow cylindrical piece of sheet material having interstices for receiving tissue growth after implantation. The primary and auxiliary terminals, respectively, are located internally and externally of the cylindrical coupling which is suitably shaped for implantation around a severed nerve ending. After implantation, the primary terminals pick up a primary signal including a desired nerve signal component and an EMG noise component while the external auxiliary terminals pick up an auxiliary signal comprising only the EMG signal. Differential combination of these signals in the output circuit provides a high quality, low noise output signal representing the desired nerve signal.

DESCRIPTION OF THE DRAWINGS

These and other objects and features of the present invention will become more apparent upon a perusal of the following description taken in conjunction with the accompanying drawings wherein.

DESCRIPTION OF THE PREFERRED EMBODIMENT

Figure 1:
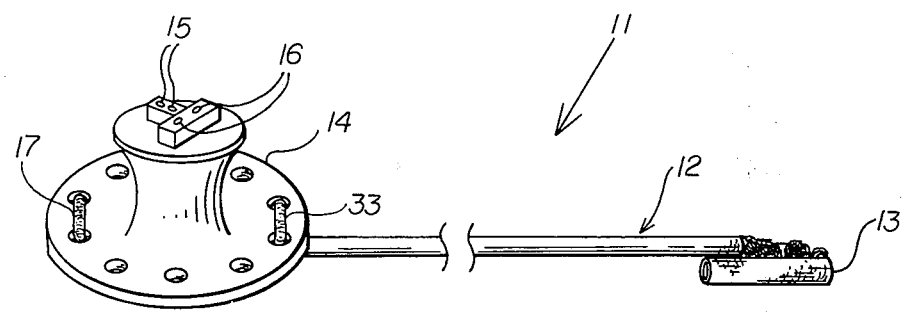
FIG. 1 is a schematic perspective view of the invention.

Referring now to FIG. 1 there is shown a device 11 for being anatomically implanted to establish electrical interface to a nerve (not shown). The device 11 includes a flexible cable 12 terminating with an input coupling 13 for accommodating the interfaced nerve. Attached to the opposite end of the cable 12 is a button 14 that supports two pairs of output terminals 15 and 16 suitable for connection to electrical measuring and recording instruments.

Figure 2:
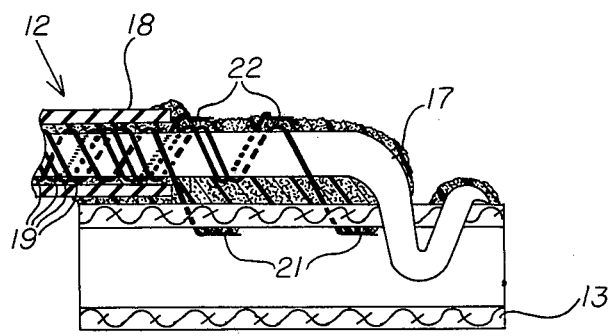
FIG. 2 is an enlarged view of an input portion of the device shown in FIG. 1.
Figure 3:
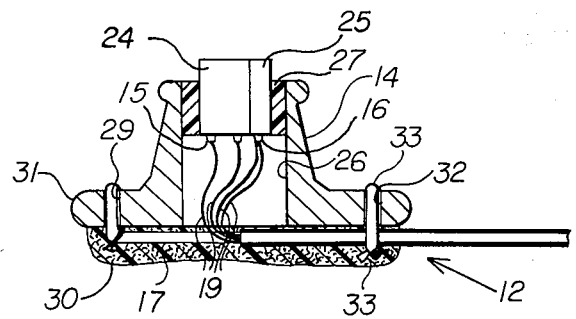
FIG. 3 is an enlarged view of an output portion of the device shown in FIG. 1.

As shown in FIGS. 2 and 3, the cable 12 comprises an elongated core 17 that extends between the input coupling 13 and the button 14 and is enclosed by a hollow cylindrical casing 18. The casing 18 is formed of a flexible material suitable for anatomic implantation while the core 17 comprises a flaccid, nonelastic thread also suited for anatomic implantation. Helically wound around and along the length of the thread 17 between the coupling 13 and the button 14 are two pairs of electrical leads 19 also formed of materials suitable for implantation. Clearance is provided between the inner wall of the casing 18 and the leads 19 so as to permit longitudinal movement thereof on the core thread 17.

As shown most clearly in FIG. 2 the coupling 13 is a hollow cylinder formed from a woven piece of sheet material again suitable for implantation. Two of the leads 19 extend through interstices of the cylindrical coupling 13 and terminate in a pair of spaced apart input electrodes 21. Also extending into and then out of the cylindrical coupling 13 through interstices therein is the core thread 17. At the ends of the other two electrical leads 19 is a second pair of input terminals 22 positioned outside the cylindrical coupling 13. As more clearly illustrated in the detailed view of FIG. 4, one of the input electrodes 21 is formed by a flattened end portion of one of the electrical leads 19 that extends out of an electrically insulative coating 20. The other electrode 21 and the electrodes 22 are identically formed. Securing together the outside surface of the cylindrical coupling 13 and the ends of the casing 18, the electrical leads 19, and the core thread 17 is a body of bonding material again suitable for implantation.

As shown most clearly in FIG. 3, molded bases 24 and 25 of the output terminals 15 and 16 are bonded within a hollow cavity 26 in the button 14 by a suitable adhesive 27. Connected to the output terminals 15 within the cavity 26 are the opposite ends of the electrical leads 19 connected to the input terminals 21 while the other output terminals 16 are connected to the electrical leads 19 terminating with the second pair of input terminals 22. The end of the core thread 17 opposite the coupling 13 extends through and is tied between a pair of openings 29 in a flanged portion 31 of the button 14. Similar openings 32 in the flanged portion 31 accommodate a thread 33 that is tied around so as to secure the cable 12 to the button 14.

It will be appreciated that the actual relative dimensions of the individual components shown in FIGS. 1–4 have been modified in the interest of providing a better understanding of the physical relationships existing therebetween.

EXAMPLE OF CONSTRUCTION AND MATERIALS

Figure 4:
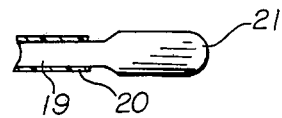
FIG. 4 is an enlarged view of one of the electrodes shown in FIG. 2.
Figure 5:
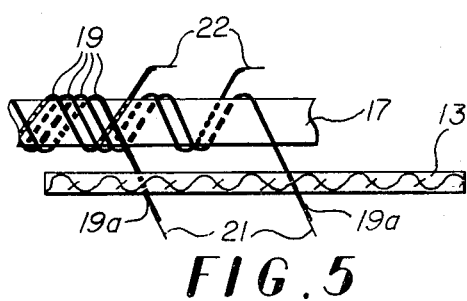
FIG. 5 is a schematic view of the device in views 1–4 at one step of its construction.
Figure 6:
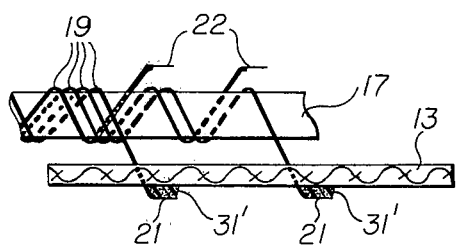
FIG. 6 is a schematic view of the device in views 1–4 at one step of its construction.
Figure 7:
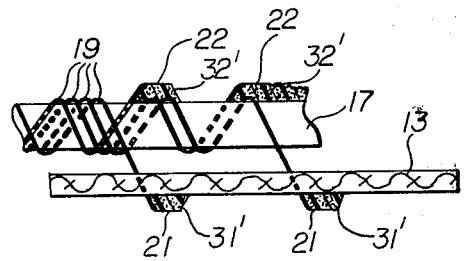
FIG. 7 is a schematic view of the device in views 1–4 at one step of its construction.
Figure 8:
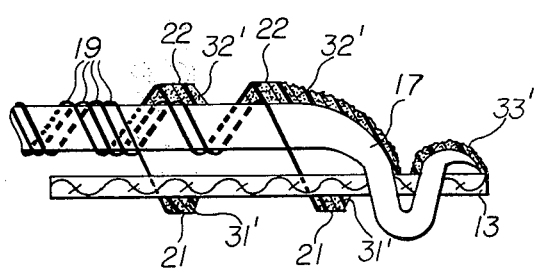
FIG. 8 is a schematic view of the device in views 1–4 at one step of its construction.

Construction of a specific implant device 11 was accomplished in the following manner: A 26 cm length of surgical silk (sold by Deknatel, Inc., Queens Village, N.Y., code 113-4, black braided, 2-0) was cut to provide the core thread 17. Next the leads 19 were prepared by cutting to a nominal length of 20 cm four 90% platinum, 10% iridium wires (0.077 mm diameter with a 0.013 mm thick coating of Teflon insulation 20 sold by Medwire Corporation, 121, S. Columbus Avenue, Mt. Vernon, N.Y.). Each of the four wire leads 19 were then tightly wound around a 14 cm mid-length portion of the thread 17 as shown in FIGS. 2 and 5. Two of the four wire leads 19 were bent as shown in FIG. 5 to provide end portions 19a extending transversely from the silk thread 17 and spaced 5 cm apart. The end portions 19a were cut to a length of approximately 0.5 mm from the silk thread 17 and their ends flattened as shown in FIG. 4 to provide the electrodes 21 with a surface area of approximately $0.036$ mm$^2$. Next, the ends of two remaining wire leads 19 were identically flattened to form the electrodes 22 which were bent parallel to the thread 17 and positioned transversely opposite the electrodes 21 as shown. A 1.5 cm by 1.2 cm piece of woven Teflon (sold by United States Catheter and Instrument Corporation as No. 3106, 0.25 mm thick) was positioned adjacent the thread 17 with the length and ribs of the material running longitudinally. Next, the two flattened electrodes 21 were pushed through the longitudinal center line of the coupling 13 at distances of 0.5 cm from opposite edges thereof and the flattened electrodes 21 were bent parallel to the plane of the coupling sheet 13 as shown in FIG. 6. The electrodes 21 were then secured to the coupling 13 by sparingly applying an epoxy mixture 31' of 1.5 cc of Hysol C8-W795 casting compound and 0.4 cc of Hysol HW-796 hardener (both components sold by Hysol Division, The Dexter Corporation, Olean, N.Y.) after which adhesive 32' (Dow Corning Company's Type 890 Silastic) was applied underneath and around the outer electrodes 22 (FIG. 7) with care being taken not to cover the outer surfaces thereof. After weaving the silk thread 17 through the cloth coupling 13, the end thereof was secured to the outside of the coupling with Dow Corning's 890 Silastic adhesive 33' as shown in FIG. 8. Finally, a 13 cm length of the casing 18 (Dow Corning Company's Silastic tubing No. 602-151, I.D. 0.64 mm, O.D. 1.2 mm) was slid over the helical wound leads 19 and secured to the coupling with Dow Corning's 890 Silastic adhesive. That substance was applied also to the junction of silk thread 17 and Teflon cloth 13 and used to fill the Silastic tube 18 at the other end of the cable 12 thereby completing a seal of the cable 12.

Figure 9:
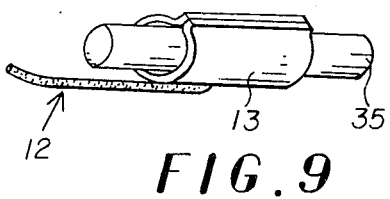
FIG. 9 is a schematic view of the device in views 1–4 at one step of its construction.

The molded terminals 15 and 16 (Model GF-2 connectors sold by Microtech, Inc., Folcroft, Pa.) were placed in the button 14 (bioCarbon 3 × 8 mm carbon button sold by Bentley Laboratories, Inc., Irvine, Calif.) and the cavity 26 filled 1 mm deep with Hysol Division's epoxy as shown in FIG. 3. Next, a 1 mm length of the insulation 20 was stripped from the free ends of the lead wires 19 each of which then was soldered to an appropriate connector pin of the electrodes 15 and 16. Next the end of the silk thread 17 was tied between the small holes 29 in the flared base 31 of the button 14 so as to eliminate any slack between the input and output electrodes. The cable 12 also was secured with a suture 33 to the openings 32 as shown in FIG. 3. Finally, the Teflon cloth 13 containing the electrodes 21 was placed around a 2 mm diameter mandrel 35 (FIG. 9) forming a tube. Down Corning's 890 Silastic adhesive was applied to bond the joined edges of the cloth 13 in place. The finished device 11 was then ready for implantation after being steamed in an autoclave for 30 minutes at 250° F.

IMPLANTATION PROCEDURE

The device has been successfully implanted in New Zealand white rabbits (3.5–4 Kg) which were anesthetized with 1.25 cc of Diabutal introduced intravenously. Anesthesia was sustained by administering ether by the open or drop method. The hind legs and buttocks were shaved and surgically prepared with Betadine solution. An incision was made in the popliteal fossa (behind the knee joint) of the hind leg so as to expose the common peroneal nerve. After severing the nerve as distally as possible near its insertion into the peroneal muscle a silk suture was passed through the distal end of the nerve. The suture and the nerve then were pulled through the sterilized tube 13 until the tube was located over the distal part of the nerve. The suture was tied to a tie on the distal part of the tube 13, thus securing the unit 11 to the nerve. The implanted unit 11 and nerve then were relocated in the popliteal fossa.

The transcutaneous button connector 14 was pushed between the skin and muscles towards the upper part of the leg until it rested on top of the gluteal muscles in the thigh. A circular incision was made on the skin above the button 14, sufficiently large to allow the electrodes 15 and 16 on the top of the button to pass through. The button 11 was then sutured to the skin through the holes provided in the bottom flange 31. With the button 14 secured in position, the incision in the popliteal fossa was closed with skin sutures.

ANATOMICAL AND HISTOLOGICAL DEVELOPMENTS

After implantation as described above, units 11 have remained in place for varying periods of up to 244 days. In most cases the enclosed nerve remained healthy and the following anatomical developments typically occurred. A capsule formed of connective tissue extending from the tissue adjacent to the implanted device 11 surrounded the tube 13. The connective tissue passed through the intersticial spaces of the tube 13 and completely filled the space between the outer surface of the nerve and the tube, firmly affixing itself to the nerve. The fibrous tissue inside and outside the tube was supplied with an abundant vascular supply that communicated through the interstitial spaces of the material forming the tube 13. The growth of the fibrous tissue inside and outside the tube anchored the electrodes 21 to the nerve and the electrodes 22 to the adjacent muscle tissue. This assured minimal relative movement between the electrodes 21 and 22 and the enclosed nerve and surrounding tissue and thereby enhanced the recording of stable nerve and EMG signals with good fidelity.

STRESS RELIEF

Another important feature of the invention is the core thread 17 that increases the useful life potential of the unit 11. By assuming any tensile forces applied between the input terminals 21 and 22 and the output terminals 15 and 16 during movement of the body portion in which the unit 11 is implanted, the thread 17 prevents the exertion of tensile stress that might rupture the extremely delicate electrical leads 19. In this way, the expected useful life of the unit is increased which is an important factor considering the intricacy of the implantation procedure.

OUTPUT SIGNAL PROCESSING

Figure 10:
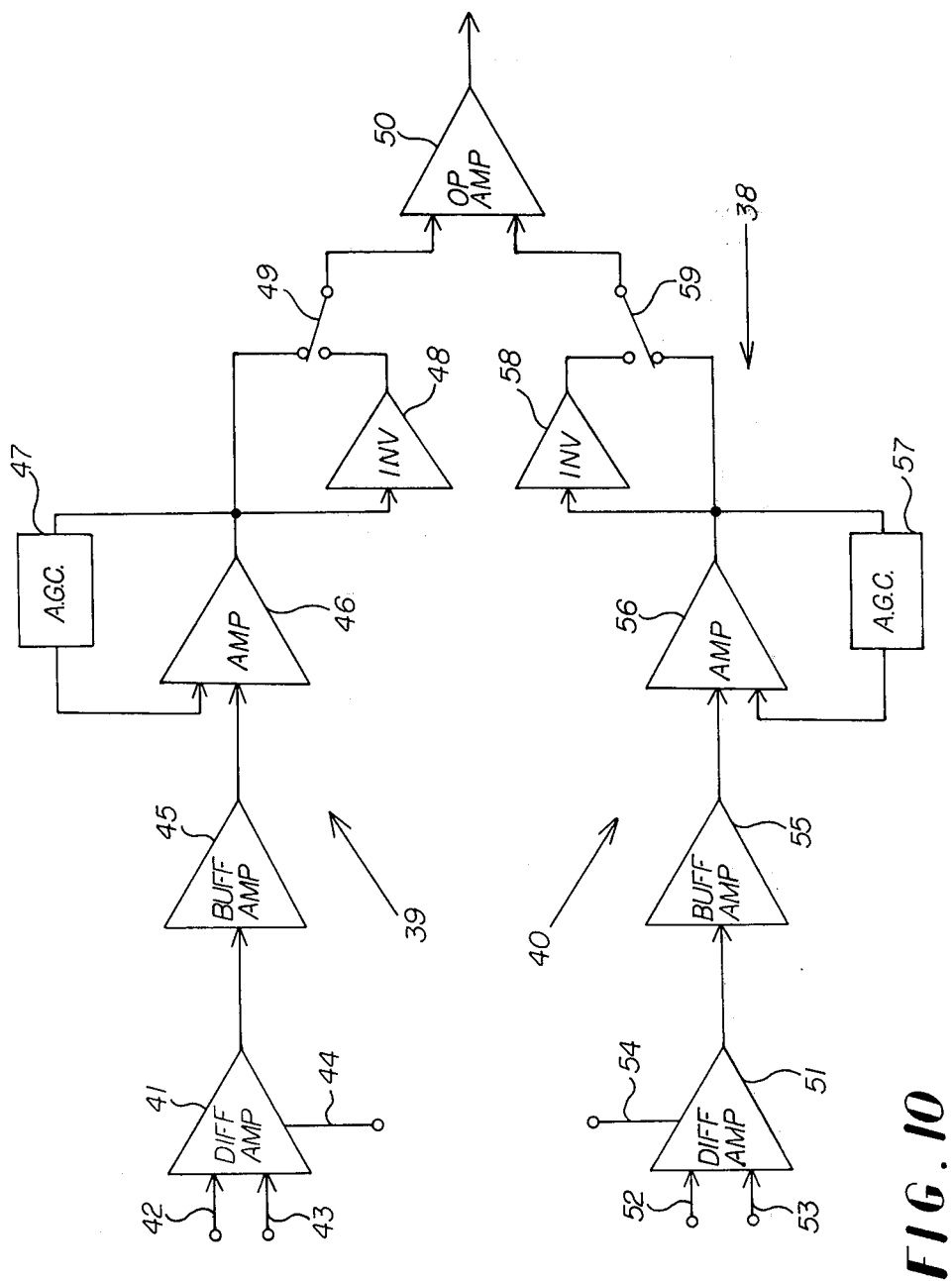
FIG. 10 is a block diagram of a signal processing circuit.

Referring now to FIG. 10 there is shown in block diagram form a discriminator network 38 for use with the device 11 shown in FIGS. 1–9 and including a primary signal channel 39 and an auxiliary signal channel 40. The primary signal channel 39 includes a differential amplifier 41 with input terminals 42 and 43 connected to the output terminals 15. Therefore the amplifier 41 receives input signals picked up by the implanted terminals 21 from the nerve ending enclosed by the tube 13. A ground terminal 44 of the differential amplifier 41 is connected to the body portion in which the device 11 is implanted. Receiving the output of the differential amplifier 41 is a buffer amplifier 45 that feeds an operational amplifier 46 provided with an automatic gain control circuit 47. The gain controlled output of the amplifier 46 is fed either through an inverter 48 to an output operational amplifier 50 or directly thereto under the control of a switch 49.

The auxiliary signal channel 40 also includes a differential amplifier 51 with input terminals 52 and 53 connected to the output terminals 16. Therefore the amplifier 51 receives the myoelectric (EMG) input signals picked up by the implanted terminals 22 from the muscle tissue around the tube 13. A ground terminal 54 of the differential amplifier 51 again is implanted. Receiving the output of the differential amplifier 51 is a buffer amplifier 55 that feeds an operational amplifier 56 provided with an automatic gain control circuit 57. The gain controlled output of the amplifier 56 is fed either through an inverter 58 to an output operational amplifier 50 or directly thereto under the control of a switch 59.

The differential amplifier 41 effects common mode rejection of the nerve signals from the input electrodes 21 thereby providing an output signal having a higher signal to noise ratio. That primary signal is amplified by the amplifiers 45 and 46 before being fed into the operational amplifier 50. Similarly, the differential amplifier 51 reduces the noise content of the EMG signals from the electrodes 22 providing a higher quality auxiliary output signal that is amplified by the amplifiers 55 and 56 before being combined with the primary nerve signal in the operational amplifier 50. The switches 49 and 59 and the inverters 48 and 58 are utilized to insure that a proper phase relationship exists between the nerve signals from channel 39 and the EMG signals from channel 40 which are differentially combined in the operational amplifier 50.

The primary signals received from the terminals 21 include a nerve component generated in the nerve enclosed by the tube 13 in addition to a substantially larger EMG component generated in the muscle tissue growth surrounding the nerve. This EMG component corresponds to the auxiliary EMG signal provided by the terminals 22 outside the tube 13. Thus, differentially combining the primary and auxiliary signals in the amplifier 50 provides a processed output signal that more sensitively represents the desired nerve signal.

Figure 11:
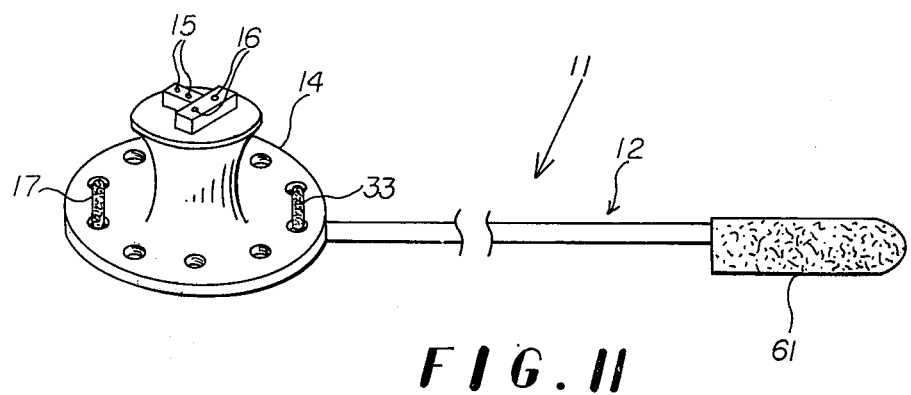
FIG. 11 is a view of a modified embodiment.
Figure 12:
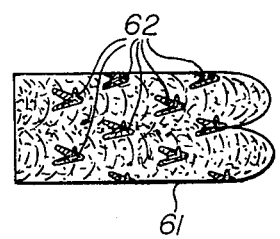
FIG. 12 is a plan view showing the cylindrical insulation of FIG. 11 after being split and flattened.

Referring now to FIG. 11 there is illustrated another embodiment of the invention which includes all the components of the embodiment shown in FIG. 1. In addition, a hollow cylindrical casing 61 with one closed end is positioned over the coupling cylinder 13 of FIG. 1. The casing 61 is formed with a thin (approximately 0.25 mm) flexible wall made of an electrically insulative material suitable for anatomic implantation such as Dow Corning Type 890 Silastic. Molded on the inner surface of the casing 61 are a plurality of projections 62 as illustrated in FIG. 12 which shows the casing longitudinally split and flattened. The projections 62 on the casing 61 engage the outer surface of the coupling cylinder 13 to maintain between the cylinder 13 and the inner walls of the casing 61 a minimum spacing of 1 mm.

The casing 61 provides an insulative shield that disrupts external electrical conductive paths to electrodes 21. Because of this shield, there is substantial reduction in the noise level of EMG signals received by the electrodes 21 from the surrounding muscle tissue. Consequently, the desired nerve signal is more easily retrieved.

Obviously, many modifications and variations of the present invention are possible in light of the above teachings. It is to be understood, therefore, that the invention can be practiced otherwise than as specifically described.

What is claimed is:

1. An electrical system for interfacing to anatomic signal sources and comprising:

terminal means suitable for anatomic implantation so as to receive primary signals generated physiologically;

coupling means comprising a piece of sheet material secured to said terminal means and being shaped and arranged for juxtaposition to the outer surface of a nerve, said sheet material having interstices of a size for receiving tissue growth after being implanted;

electrical lead means suitable for anatomic implantation and connected to said terminal means so as to receive said primary signals;

output circuit means connected to receive said primary signals from said electrical lead means; and electrical insulator means suitable for anatomic implantation and enclosing said terminal means so as to shield said terminal means from noise signals generated physiologically, said insulator means comprising an elongated hollow casing closed at one end and enclosing said coupling means and of a size to surround the nerve so as to disrupt external electrical conductive paths to said terminal means.

2. An electrical system according to claim 1 wherein said hollow casing is formed by thin, flexible walls.

3. An electrical system according to claim 2 wherein said walls are spaced at least 1 mm from said coupling means.

4. An electrical system according to claim 3 wherein said coupling means comprises a hollow cylinder of a size for surrounding the nerve, and said terminal means is disposed within said hollow cylinder.

5. An electrical system according to claim 4 wherein the inner surface of said hollow casing possesses a plurality of projections that contact the outer surface of said cylinder so as to provide said spacing.

* * * * *